United States Patent [19]

May

[11] 4,449,825

[45] May 22, 1984

[54] OPTICAL MEASURING APPARATUS EMPLOYING A LASER

[75] Inventor: Albert D. May, Toronto, Canada

[73] Assignee: The University of Toronto Innovations Foundation, Toronto, Canada

[21] Appl. No.: 272,520

[22] Filed: Jun. 11, 1981

[30] Foreign Application Priority Data

Jun. 16, 1980 [CA] Canada ................................... 354108

[51] Int. Cl.$^3$ ............................................... G01B 9/02
[52] U.S. Cl. ..................................... 356/349; 356/351
[58] Field of Search ............... 356/346, 349, 350, 351, 356/352; 372/23, 105, 106

[56] References Cited

U.S. PATENT DOCUMENTS 3,506,362 4/1970 Doyle et al. ..................... 356/351 X
3,786,681 1/1974 Kiehn .............................. 356/350 X
4,255,969 3/1981 Lautzenhiser ................... 356/349 X

OTHER PUBLICATIONS

Heckenberg et al. "Multipass Laser Interferometry for Plasma Studies", *Rev. Sci. Instru.*, vol. 42, No. 7, pp. 977-980, 7/71.
Aiken et al., "A Three-Laser Intercavity Interferometer for the Study of Low Density Plasmas", *J. Phys. D*, vol. 10, No. 12, pp. 1541-1547, 8/77.

*Primary Examiner*—William L. Sikes
*Assistant Examiner*—Matthew W. Koren
*Attorney, Agent, or Firm*—Murray & Whisenhunt

[57] ABSTRACT

The invention provides optical measuring apparatus including a laser which is arranged to have an output of electromagnetic radiation including at least two different simultaneously-generated frequencies. This output is fed to a detector, such as an optical diode, which produces a corresponding electric signal at the difference (beat) frequency. The beat frequency, any change in the beat frequency, or any rate of change of the beat frequency can now be examined electrically to the degree of accuracy generally available in that art, usually to a much higher degree than is available in the optical or mechanical arts. The parameter to be examined may be that of an element causing the production of the beat frequency such as a birefringent material, or may be that of an element which changes the frequency in some way, such as an angular orientation of two quarter-wave plates.

11 Claims, 3 Drawing Figures

OPTICAL MEASURING APPARATUS EMPLOYING A LASER

FIELD OF THE INVENTION

The present invention is concerned with improvements in or related to optical measuring apparatus employing a laser.

REVIEW OF THE PRIOR ART

There is a constant need for precise measurement of different parameters, and any substantial improvement in the degree of resolution obtainable with reasonable accuracy is welcome. Such apparatus is also of course subject to the usual economic and physical constraints that it cannot be unduly costly to manufacture and maintain, and it must be sufficiently robust to withstand normal usage.

DEFINITION OF THE INVENTION

It is an object of the invention to provide a new optical measuring apparatus employing a laser.

It is a more specific object to provide such apparatus in which a change in at least one optical parameter therein can be measured electrically.

In accordance with the present invention there is provided optical measuring apparatus comprising:

a laser having an output of corresponding electromagentic radiation;

means causing in the said output the presence of at least two different simultaneously generated frequencies of the said radiation, detector means receiving the said output and producing an electric signal representative thereof, and means for examining in the said electric signal at least a component thereof corresponding to the beat frequency between the said frequencies.

The said means causing in the said output the said different frequencies may be an element having a property to be measured by examination of the beat frequency by said detecting means, or it may comprise a mechanical element, physical movement of which causes a change in the beat frequency.

The apparatus may include means for the introduction therein of a material in the path of the electromagnetic radiation that can effect a change in the said beat frequency, wherein such change is measured by the said examining means.

DESCRIPTION OF THE DRAWINGS

Different kinds of apparatus which are particular preferred embodiments of the invention will now be described by way of example, with reference to the accompanying diagrammatic drawing, wherein.

DESCRIPTION OF THE PREFERRED EMBODIMENTS

Figure 1:
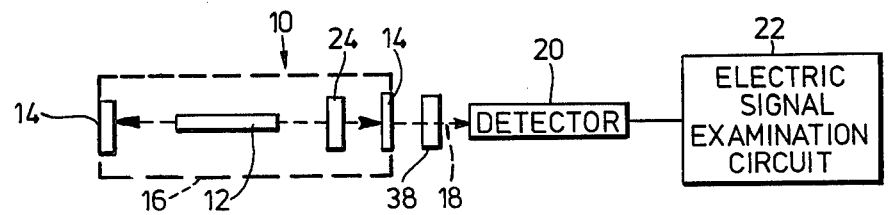
FIG. 1 illustrates one form of the apparatus in which the parameter to be measured is an optical characteristic of a solid material.

Referring now to FIG. 1, the apparatus comprises a laser 10, shown here as of linear form, consisting of a laser gain tube or generator 12 and mirrors 14 forming a cavity 16. Electromagnetic radiation 18 emitted by the laser is received by a detector 20 which produces a corresponding electric signal, which signal is fed to a signal examination circuit 22.

One use of such apparatus is the measurement of the birefringence produced by an element 24 which is introduced into the cavity in any suitable manner. Such an element upon its introduction into the laser, which is unpolarised, will produce in the radiation output two polarisation modes with a frequency difference which is proportional to the birefringence. The detector 20 may consist of a fast-acting, light-sensitive diode which, upon receipt of this output, will produce an electric signal having a frequency therein corresponding to the beat frequency resulting from the frequency difference. The circuit 22 will measure the beat frequency and provide some visible output to the operator that will be a precise measure of the birefringence. In other applications of the invention the circuit 22 may examine the change in beat frequency produced by the element 24, and/or the rate of change of that frequency and/or the frequency distribution of beat frequencies and harmonics thereof in the signal envelope.

More specifically, the insertion of element 24 into the cavity modifies the modes (standing waves) of the laser and, as described above, the modification is detected as a frequency which can then be related to the properties of the element. For illustrative purposes let $\overline{E}_o$ represent the polarization of the field inside the cavity at some point; $\overline{E}_{rt}$ represent the polarization after one round trip; and [A] represent the effect of all the polarization optics inside or part of the cavity. [A] includes explicitly the polarization properties of element 24. The relationship between $\overline{E}_{rt}$ and $\overline{E}_o$ is given by $$\overline{E}_{rt} = [A] \, \overline{E}_o \text{ tm} \quad (1)$$

and ensures a standing wave by demanding $\overline{E}_{rt} = \overline{E}_o$. In general there are two solutions for (1) corresponding to two orthogonal polarization modes for the cavity. For these polarization modes the relations $$Nc/2 = fL_{op} = fL \cdot n \quad (2)$$

may now be used to determine the difference in frequency of the two orthogonally polarized modes, where N is an integer which is considered to be fixed; c is the velocity of light; f is the frequency of the mode; $L_{op}$ is the optical length of the cavity; and n is the index of refraction. Length $L_{op}$, index n and the physical length L are related by $L_{op} = nL$. Thus if n is different for different polarizations then two different frequencies $f_1$ and $f_2$ will be produced and the difference or beat frequency $f_d$ is a measure of the difference in n. In such case the circuit 22 need only measure the beat frequency $f_d$ and consist of a frequency meter with the required degree of accuracy.

Some of the potential uses of the apparatus of the invention are to measure for example birefringence, optical homegeneity, Kerr constants, Faraday constants, Cotton-Mouton coefficients, molecular quadrupole moments and optical activity. In such applications the physical lengths of the elements are measured beforehand, so that the unknown differential effect is the index of refraction. Again in other applications it may be the length of the radiation path that is the variable parameter that is to be measured by examination of the beat frequency, such as in highly accurate linear measuring devices.

Figure 2:
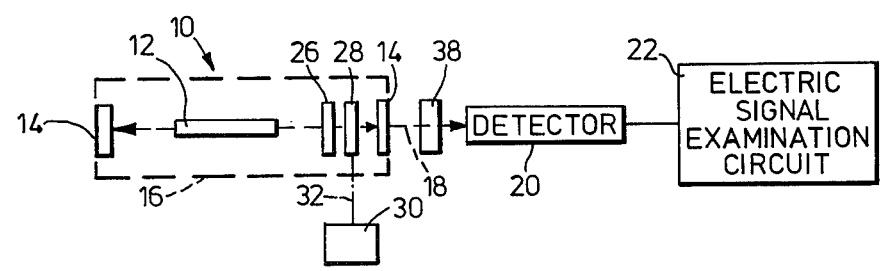
FIG. 2 illustrates another form of the apparatus in which the parameter to be measured is a physical one, specifically the relative orientation of two quarter wave plates.

Referring now to FIG. 2, in the apparatus illustrated diagrammatically therein, the optical path of the laser includes two quater-wave plates 26 and 28, the plate 26 being fixed, while the plate 28 can be moved by a mechanical operator represented by the block 30 via a mechanical connection 32. Such apparatus relies instead upon the properties of [A]. The exact form of [A] depends not only upon the polarization optics, but also upon their relative orientation. As a consequence the polarization modes and frequencies change with a change in the relative orientations of the components. For example with the illustrated plates 26 and 28 inside the cavity the beat frequency will change by $C/2L$ for 90° relative rotation. Thus the measurement of angle, change of angle or rate of change of angle is altered to respectively the measurement of frequency in an electric signal, measurement of change of frequency and measurement of rate of change of frequency, all of which can be done relatively inexpensively with a high degree of accuracy.

Some potential applications for this form of the apparatus are for example gravitational gradient meters for geophysical exploration, accelerometers and navigational aids, all of which can be made to function with measurements of this kind.

In the first class of embodiments of the invention, as illustrated by FIG. 1, the differences being measured are not strong functions of the frequency so that the fact that the laser actually operates on two frequencies does not distort the measurement, i.e. the effect is "flat" with frequency. If the laser is arranged to operate inherently with at least two frequencies simultaneously, then insertion into the cavity of a material with dispersion will cause the beat frequency to change. It is not necessary that the different frequencies be associated with different polarizations; they could be associated with the same polarization mode but with different longitudinal modes (different values of N in equation (2)), or with different transverse modes. An example of the application of such apparatus would be for pollution monitoring, where one would insert the material to be monitored and detect the resonant dispersion, rather than resonant absorption as is the common way presently employed in such equipment.

Figure 3:
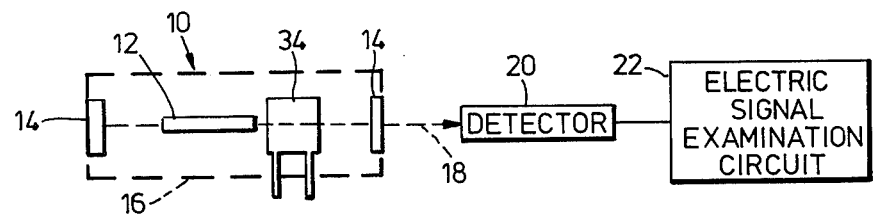
FIG. 3 illustrates a further form in which the parameter to be measured is an optical characteristic of a fluid, such as dispersion in the index of refraction of a gas.

An example of such apparatus is illustrated by FIG. 3 which includes a cell 34 in the laser cavity. The fluid material whose dispersion is to be measured is fed into the cell, or through the cell on a continuous basis, as required, while the resultant electric signal is examined for the characteristic that will indicate the level of the pollutant to be detected. It is found by analysis that in such apparatus a sensitivity greatly in excess of 1 part in $10^9$ may be achieved, i.e. in excess of that obtainable with current technology in which the cell is outside the laser.

Each of the different apparatuses described above may also require the provision of an additional polarizing element 38, which may be internally or externally of the cavity, for the purpose for example of obtaining a beat frequency within a preferred range or to facilitate its subsequent examination in the circuit 22.

For the purpose of simplifying and clarifying the explanation of the operation of apparatus of the invention simple rather than general examples have been described. For example a linear laser is illustrated but in some applications a ring laser may be preferred. For the same reason, the polarization and frequency problems have been treated separately, but in general equations (1) and (2) must be combined and solved simultaneously. Moreover, the element 24 has been treated as a single polarization element, but for technical reasons one may often require the element to consist of one part of fixed polarization property and at least one other part consisting of a cell or device whose properties are to be measured. The advantages of precision or sensitivity arises with the apparatus of the invention because a beat frequency between two simultaneously generated frequencies is measured and this beat frequency is very sharp, of the order of the intrinsic width of the laser. Mechanical vibrations of the laser will change L and thus f, but it can be shown that $f_1-f_2$ will not change; thus there is a correlation in the shifts of $f_1$ and $f_2$ so that the beat is sharp.

A specific form of the apparatus of the invention consisting of a gravity gradient meter as used, for example, for geophysical exploration, uses a double polorization laser consisting of a linear cavity with two quarter-wave plates inside the cavity along with a helium-neon gain tube with flat anti-reflection coated windows. The fundamental beat between the two polarization modes depends upon the angle between, say, the two fast axes of the quarter-wave plates, and it varies from O to $C/2L$ hertz as the plates are rotated relative to one another from an orientation in which their axes are parallel to one in which they are perpendicular. One way of achieving the required structure is to mount one of the plates so that it can rotate about an axis, and to attach a dumbell arrangement to it so that the suspension is sensitive to gradients in the gravational field. It is believed that the resultant device is of the order of 10 to 100 times more sensitive than commercial equipment available to date. The invention is also applicable to other forms of device in which angle, change of angle or rate of change of angle is to be measured.

The embodiments of the invention in which an exclusive property or privilege is claimed are defined as follows:

1. Optical measuring apparatus comprising:
   laser, including a laser gain tube;
      exciting means for exciting a laser beam to be produced by the gain tube, said laser beam having a laser beam axis;
      reflecting means located opposite respective ends of the gain tube;
      the reflecting means and the laser gain tube forming a laser cavity, the laser being tunable by the exciting means to provide at least two orthogonal polarization modes of the laser beam, said modes each having a frequency;
      optical means locatable within the laser cavity between one end of the laser gain tube and one of the reflecting means, the optical means comprising at least two spaced quarter-wave plates located substantially perpendicular to the laser beam axis, at least one of the quarter-wave plates being rotatable relative to the other quarter-wave plate substantially about the laser beam axis, the polarization modes passing through the optical means and the laser cavity and forming a laser cavity output;

detector means for receiving the laser cavity output and providing a corresponding electrical signal;

signal examination means connected to the detector means for receiving and processing the electrical signal;

whereby, in use, the at least one rotatable quarter-wave plate is rotated relative to the other quarter-wave plate about the laser beam axis in response to a physical parameter being measured, the relative rotation between the quarter-wave plates causing the polarization modes and frequencies of the polarization modes to change, the different frequencies being detected and processed to provide a beat signal which is a direction function of the physical parameter being measured.

2. Optical measuring apparatus as claimed in claim 1, wherein there are two orthogonal polarization modes.

3. Optical measuring apparatus as claimed in claim 1 or 2, wherein the quarter-wave plates are disc-shaped.

4. Optical measuring apparatus as claimed in claim 3, wherein the quarter-wave plate furthest from the laser gain tube is rotatable.

5. Optical measuring apparatus as claimed in claim 1, wherein the signal examination means measures a value selected from a group consisting of the value of the frequency, the change in value of the frequency, and the rate of change in the value of the beat frequency.

6. Optical measuring apparatus comprising:
a single laser, including a laser gain tube;
exciting means for exciting a laser beam to be produced by the gain tube;
reflecting means located opposite respective ends of the gain tube, the reflecting means and the laser gain tube forming a laser cavity, said laser cavity having a laser cavity output;
the laser being tunable by the exciting means to provide two modes with at least two simultaneous frequencies;
optical means comprising a chamber located in the laser beam and communicating with the exterior of the cavity by an inlet and an outlet port, a material whose dispersion is to be measured being receiveable in said chamber;
detector means for receiving the laser cavity output and providing a corresponding electrical signal;
beat frequency signal measuring means for receiving the electrical signal from said detector means and for processing said electrical signal to provide a beat frequency signal which is a function of the dispersion of a material in the chamber;
whereby, in use, a material whose dispersion is to be measured is entered into the chamber thereby changing at least one mode of frequency to give a frequency difference, the frequency difference being detected and processed to provide said beat frequency signal which is a function of the dispersion of the material in the chamber.

7. Optical measuring apparatus as claimed in claim 6, wherein the different frequencies are associated with different polarization modes.

8. Optical measuring apparatus as claimed in claim 6, wherein the different frequencies are associated with the same polarization modes and are associated with modes selected from the group consisting of different longitudinal modes and different transverse modes.

9. Optical measuring apparatus as claimed in claim 1 or 6, wherein polarizing means are provided, said polarizing means being locatable in positions selected from the group consisting of internal positions and external positions of the cavity.

10. A gravity gradient meter, comprising:
a laser, including a laser gain tube;
exciting means for exciting a laser beam to be produced by the gain tube, said laser beam having a laser beam axis;
reflecting means located opposite respective ends of the gain tube;
the reflecting means and the laser gain tube forming a laser cavity;
the laser being tunable by the exciting means to provide at least two orthogonal polarization modes of the laser beam;
optical means locatable within the laser cavity between one end of the laser gain tube and one of the reflecting means, the optical means comprising two quarter-wave plates located substantially perpendicular to the laser beam axis, one of the plates being mounted so that it can rotate about the laser beam axis, the polarization modes passing through the quarter-wave plates and the laser cavity and forming the laser cavity output;
detector means for receiving the laser cavity output and providing a corresponding electrical signal;
signal examination means for receiving and processing the electrical signal;
suspension means connectable to the rotatable plate so that said rotatable plate is rotatable about an axis, said suspension means being sensitive to gravitational field gradients.

11. A gravity gradient meter as claimed in claim 10, wherein the laser gain tube is a helium-neon gain tube with flat anti-reflection coated windows.

* * * * *